United States Patent [19]
Kanno et al.

[11] Patent Number: 6,005,112
[45] Date of Patent: Dec. 21, 1999

[54] PROCESS FOR PRODUCING PYRIDINECARBOXAMIDES OR THIOCARBOXAMIDES

[75] Inventors: Hisashi Kanno, Fukushima; Yoshikazu Kubota, Chiba, both of Japan

[73] Assignee: Kureha Kagaku Kogyo Kabushiki Kaisha, Japan

[21] Appl. No.: 09/091,731

[22] PCT Filed: Dec. 26, 1996

[86] PCT No.: PCT/JP96/03806

§ 371 Date: Aug. 12, 1998

§ 102(e) Date: Aug. 12, 1998

[87] PCT Pub. No.: WO97/24329

PCT Pub. Date: Jul. 10, 1997

[30] Foreign Application Priority Data

Dec. 28, 1995 [JP] Japan ................................. 7-353264
May 10, 1996 [JP] Japan ................................. 8-140720

[51] Int. Cl.$^6$ .................... C07D 213/81; C07D 213/82; C07D 213/83
[52] U.S. Cl. ............................................. 546/313; 546/323
[58] Field of Search ...................................... 546/313, 323

[56] References Cited

U.S. PATENT DOCUMENTS 3,505,344  4/1970  Kelyman ................................. 546/291
4,270,946  6/1981  Gutman ................................... 546/291

FOREIGN PATENT DOCUMENTS 50-13312    2/1975   Japan.
55-69518    5/1980   Japan.
1-102064    4/1989   Japan.
4-217959    8/1992   Japan.
4-290805   10/1992   Japan.

*Primary Examiner*—Zinna Northington Davis
*Attorney, Agent, or Firm*—Nixon & Vanderhye

[57] ABSTRACT

A process for producing N-substituted pyridine carboxamide or thiocarboxamide, comprising reacting a substituted or unsubstituted pyridine metal compound with substituted isocyanate or isothiocyanate to obtain an addition reaction product thereof, and then substituting the metal of said addition reaction product with a proton. The process according to the present invention can be applied even to compounds having an oxidation-susceptible substituent group and, therefore, industrially useful.

3 Claims, No Drawings

PROCESS FOR PRODUCING PYRIDINECARBOXAMIDES OR THIOCARBOXAMIDES

This application is a 371 application of PCT/JP96/03806 filed Dec. 26, 1996.

TECHNICAL FIELD

The present invention relates to a process for producing N-substituted pyridine carboxamide or thiocarboxamide, and more particularly, it relates to an industrially useful process for producing N-substituted pyridine carboxamide or thiocarboxamide.

BACKGROUND ART

It is known that N-substituted-6-pyridine carboxamide or thiocarboxamide has a herbicidal activity, as described, for example, in Japanese Patent Application Laid-open (KOKAI) No. 4-290805, U.S. Pat. No. 4,270,946 or the like. As the most ordinary method for producing the above-mentioned compounds, there is known a method comprising producing a carboxylic acid, halogenating the carboxylic acid and then reacting the halogenated carboxylic acid with amine. In the above Japanese Patent Application Laid-open (KOKAI) No. 4-290805, it is described that pyridine carboxylic acid is produced by such an oxidation reaction of methyl pyridine as described in "J. Pharm. Belg." (1980), 35, 1, 5–11.

However, it has been difficult to produce the pyridine carboxylic acid having an oxidation-susceptible substituent group bonded to a pyridine ring thereof, such as an alkyl group, an amino group or a group having thiol ether bond, by the oxidation reaction such as oxidation of a methyl group with a high yield.

In addition, there is conventionally unknown any method of producing N-substituted pyridine thiocarboxamide without sulfidization of N-substituted pyridine carboxamide, until the process according to the present invention has been proposed herein by the present inventors.

The present invention has been attained in view of the above-mentioned problems. It is an object of the present invention to provide a industrially useful process for producing N-substituted pyridine carboxamide or thiocarboxamide, which can reduce limitations to production thereof.

As a result of the present inventors' earnest studies concerning a novel process for the production of N-substituted pyridine carboxamide or thiocarboxamide, it has been found that by reacting a pyridine metal compound and substituted isocyanate (or isothiocyanate) with each other, the aimed products, even N-substituted pyridine carboxamide having an oxidation-susceptible substituent group, can be produced with a high yield, and N-substituted pyridine thiocarboxamide can be produced with a high yield without sulfidization of N-substituted pyridine carboxamide. The present invention has been attained on the basis of the finding.

DISCLOSURE OF THE INVENTION

That is, in an aspect of the present invention, there is provided a process for producing N-substituted pyridine carboxamide or thiocarboxamide, comprising reacting a pyridine metal compound with substituted isocyanate (or thioisocyanate) to obtain an addition reaction product thereof, and then substituting the metal of the addition reaction product with a proton.

The present invention is described in detail below. In the present invention, N-substituted pyridine carboxamide or thiocarboxamide can be usually produced by reacting a pyridine metal compound with a substituted isocyanate or thioisocyanate (in the present specification, which means not only compounds expressed by the terminology "substituted isocyanate or thioisocyanate", especially those represented herein by the specific chemical formulae, but also compounds to which at least one isocyanate or thioisocyanate group is bonded) to obtain an addition reaction product thereof, and then substituting the metal of the addition reaction product with a proton. The above-mentioned pyridine metal compound and substituted isocyanate or thioisocyanate are not limited to particular ones as far as N-substituted pyridine carboxamide or thiocarboxamide can be produced therefrom by the process according to the present invention.

As the substituent groups of the above-mentioned pyridine metal compounds, there may be usually exemplified a halogen atom, an alkyl group, a haloalkyl group, an alkoxy group, a haloalkoxy group, an alkylthio group, a haloalkylthio group, a dialkylamino group, a (substituted or unsubstituted)phenoxy group, a (substituted or unsubstituted)phenylthio group, a di(substituted or unsubstituted phenyl)amino group, an alkyl{(substituted or unsubstituted)phenyl)}amino group, an alkyl{(substituted or unsubstituted)phenylalkyl}amino group, a {(substituted or unsubstituted)phenyl} or {{(substituted or unsubstituted) phenyl}alkyl}amino group or the like.

As the metals of the above-mentioned pyridine metal compounds, there may be usually exemplified alkali metals such as lithium, sodium or potassium; alkali earth metals such as magnesium; alkali earth metal halogen; copper alkali metal; copper alkali earth metal halogen; or the like.

The production process according to the present invention can be shown by the following reaction formula (1).

The N-substituted pyridine carboxamide or pyridine thiocarboxamide represented by the formula (I) can be produced by reacting the pyridine metal compound represented by the formula (II) with the substituted isocyanate (or isothiocyanate) represented by the formula (III) to form a carbon-carbon bond between a carbon atom of pyridine ring and that of the substituted isocyanate (or isothiocyanate) and obtain an addition reaction product thereof, and then substituting the metal of the addition reaction product with a proton.

The above-mentioned substitution of the metal with a proton may be carried out by treating the obtained addition reaction solution with an aqueous acid solution. This reaction is shown by the following reaction formula (1).

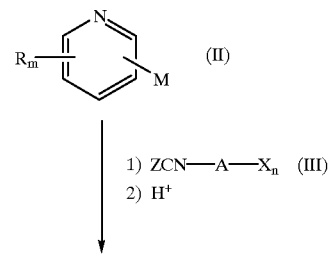

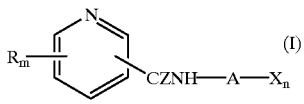

wherein
R is a hydrogen atom, a halogen atom, an alkyl group, a haloalkyl group, an alkoxy group, a haloalkoxy group, an alkylthio group, a haloalkylthio group, a dialkylamino group, a (substituted or unsubstituted)phenoxy group, a (substituted or unsubstituted)phenylthio group, a di{(substituted or unsubstituted)phenyl}amino group, an alkyl{(substituted or unsubstituted)phenyl}amino group, an alkyl{(substituted or unsubstituted)phenylalkyl}amino group or a {(substituted or unsubstituted)phenyl} {{(substituted or unsubstituted)phenyl}alkyl}amino group;

m is an integer of 0 to 4, and when m is an integer of not less than 2, Rs are the same or different;

A is an alkyl group, an alkenyl group, an alkynyl group, a cycloalkyl group, a cycloalkylalkyl group, a phenyl group or an aralkyl group;

X is a halogen atom, an alkoxy group, a haloalkoxy group, an alkylthio group, an alkyl group, a haloalkyl group or a di(alkyl)amino group;

n is 0 to an integer selected from numbers of hydrogen atoms which can be substituted with hydrocarbon groups, and when n is an integer of not less than 2, Rs may be the same or different;

Z is an oxygen atom or a sulfur atom; and

M is alkali metal, alkali earth metal-Q wherein Q is a halogen atom, or ½(Cu-alkali metal).

Next, the definition of A used in the present specification are explained below.

The chain-like hydrocarbon moiety of A is constituted by a longest carbon chain as a main chain exclusive of alkyl groups bonded as side chains to the main chain, and the alkyl groups as side chains are regarded as substituents X.

That is, in the case of alkyl groups, the longest carbon chain thereof is regarded as A, and the groups bonded thereto are regarded as substituents. Accordingly, in the case of isopropyl group, an ethyl group is regarded as A and a methyl group bonded to the 1-position of the ethyl group is regarded as a substituent. Similarly, in the case of t-butyl group, an ethyl group is regarded as A, and two methyl groups bonded to the 1-position thereof are regarded as substituents.

In the case of alkenyl group, the carbon chain from the carbon atom bonded to a nitrogen atom of 2-CZN of pyridine up to the double bond located at the furthest position therefrom, is regarded as A, and the alkyl groups bonded as side chains to A are regarded as substituents X.

In the case of alkynyl group, the carbon chain from the carbon atom bonded to a nitrogen atom of 2-CZN of pyridine up to the triple bond located at the furthest position therefrom, is regarded as A, and the alkyl groups bonded as side chains to A are regarded as substituents X.

In the case where both the double and triple bonds are included in A, the carbon chain from the carbon atom bonded to a nitrogen atom of 2-CZN of pyridine up to the multiple bond located at the furthest position from the 1-position thereof, is regarded as A, and the alkyl groups bonded as side chains to A are regarded as substituents x.

In the case where A is an alkyl group, an alkoxy group, an alkylamino group or a dialkylamino group, the substituent group X is not bonded to the terminal position of A.

R may include the following specific substituents:

Halogen atoms such as fluorine, chlorine, bromine or iodine;

Alkyl groups, usually $C_1$ to $C_{10}$ alkyl groups, for example, $C_1$ to $C_4$ alkyl groups such as methyl, ethyl, 1-methylethyl, propyl or the like;

Haloalkyl groups, usually $C_1$ to $C_{10}$ haloalkyl groups, for example, $C_1$ to $C_4$ haloalkyl groups such as trifluoromethyl or 1,1,2,2,2-pentafluoroethyl;

Alkoxy groups, usually $C_1$ to $C_{10}$ alkoxy groups, for example, $C_1$ to $C_4$ alkoxy groups such as methoxy, ethoxy or propoxy;

Haloalkoxy groups, usually $C_1$ to $C_{10}$ haloalkoxy groups, for example, $C_1$ to $C_4$ haloalkoxy groups such as 2,2,2-trifluoroethoxy;

Alkylthio groups, usually $C_1$ to $C_{10}$ alkylthio groups, for example, $C_1$ to $C_4$ alkylthio groups such as methylthio or ethylthio;

Haloalkylthio groups, usually $C_1$ to $C_{10}$ haloalkylthio groups, for example, $C_1$ to $C_4$ haloalkylthio groups such as 2,2,2-trifluoroethylthio;

Dialkylamino groups, usually di($C_1$ to $C_{10}$ alkyl)amino groups, for example, di($C_1$ to $C_4$ alkyl)amino groups such as dimethylamino, diethylamino or ethylmethylamino;

Phenoxy group;

Phenylthio group;

diphenylamino groups;

(Alkyl)(phenylalkyl)amino groups, usually ($C_1$ to $C_{10}$ alkyl) (phenyl $C_1$ to $C_5$ alkyl)amino groups, for example, ($C_1$ to $C_4$ alkyl) (phenyl $C_1$ to $C_3$ alkyl)amino groups such as methyl(phenylmethyl)amino, methyl(phenylethyl)amino or ethyl(phenylmethyl)amino;

Alkyl(phenyl)amino groups, usually ($C_1$ to $C_4$ alkyl) (phenyl)amino groups, for example, methyl(phenyl)amino, ethyl(phenyl)amino or propyl(phenyl)amino; or (Phenyl)(phenylalkyl)amino groups, usually (phenyl) (phenyl $C_1$ to $C_5$ alkyl)amino groups, for example, phenyl(phenyl $C_1$ to $C_3$ alkyl)amino groups such as phenyl(phenylmethyl)amino or phenyl(phenylethyl)amino.

As the substituents bonded to a benzene ring of phenyl of R, there may be exemplified the following substituents: halogen atoms, alkyl groups, haloalkyl groups, alkoxy groups, haloalkoxy groups, alkylthio group, haloalkylthio groups, dialkylamino groups, a phenoxy group, a phenylthio group, a diphenylamino group, alkyl(phenyl)amino groups, alkyl(phenylalkyl)amino groups or {{substituted or unsubstituted)phenyl}alkyl}amino groups.

As the substituents bonded to a benzene ring of phenyl of R, there may be exemplified the following substituents: halogen atoms such as fluorine, chlorine, bromine or iodine; alkyl groups, usually $C_1$ to $C_{10}$ alkyl groups; haloalkyl groups, usually $C_1$ to $C_{10}$ haloalkyl groups; alkoxy groups, usually $C_1$ to $C_{10}$ alkoxy groups; haloalkoxy groups, usually $C_1$ to $C_{10}$ haloalkoxy groups; alkylthio group, usually $C_1$ to $C_{10}$ alkylthio groups; haloalkylthio groups, usually $C_1$ to $C_{10}$ haloalkylthio groups; dialkylamino groups, usually di($C_1$ to $C_{10}$ alkyl)amino groups; a phenoxy group; a phenylthio group; a diphenylamino group; alkyl(phenyl)amino groups, usually ($C_1$ to $C_{10}$ alkyl)(phenyl)amino groups; alkyl(phenylalkyl)amino groups, usually ($C_1$ to $C_{10}$ alkyl) (phenyl $C_1$ to $C_5$ alkyl)amino groups; or phenyl (phenylalkyl)amino groups, usually (phenyl)(phenyl $C_1$ to $C_5$ alkyl)amino groups.

As the preferred substituents bonded to the phenyl of R, there may be respectively exemplified: as the halogen atoms, fluorine, chlorine or bromine; as the alkyl groups, $C_1$ to $C_4$ alkyl groups, for example, methyl, ethyl or propyl; as the haloalkyl groups, $C_1$ to $C_4$ haloalkyl groups, for example, trifluoromethyl or 1,1,2,2,2-pentafluoroethyl; as the alkoxy groups, $C_1$ to $C_4$ alkoxy groups, for example, methoxy, ethoxy or propoxy; as the haloalkoxy groups, $C_1$ to $C_4$ haloalkoxy groups, for example, trifluoromethoxy, difluoromethoxy, 2,2,2-trifluoroethoxy or 2,2,3,3,3-pentafluoropropoxy; as the alkylthio groups, $C_1$ to $C_4$ alkylthio groups, for example, methylthio or ethylthio; as the haloalkylthio groups, $C_1$ to $C_4$ haloalkylthio groups, for example, trifluoromethylthio; as the dialkylamino groups, di($C_1$ to $C_4$ alkyl)amino groups, for example, dimethylamino, diethylamino or ethylmethylamino; a phenyl group; a phenoxy group; a phenylthio group; a diphenylamino group; as the (alkyl)(phenyl)amino groups, ($C_1$ to $C_4$ alkyl)(phenyl)amino groups, for example, methylphenylamino, ethylphenylamino or propylphenylamino; as the (alkyl) (phenylalkyl)amino groups, ($C_1$ to $C_4$ alkyl) (phenyl $C_1$ to $C_3$ alkyl)amino groups, for example, methyl(phenylmethyl)amino, methyl(phenylethyl)amino or ethyl(phenylmethyl)amino; and as the (phenyl) (phenylalkyl)amino groups, (phenyl)(phenyl $C_1$ to $C_3$ alkyl) amino groups, for example, phenyl(phenylmethyl)amino or phenyl(phenylethyl)amino. phenyl($C_1$ to $C_3$ alkyl) groups (indicating such arylalkyl groups whose alkyl moiety has 1 to 3 carbon atoms and whose aryl group is phenyl) such as phenylmethyl, phenylethyl, phenylpropyl or the like;

As the more preferred substituents bonded to the phenyl of R, there may be respectively exemplified: as the halogen atoms, fluorine or chlorine; as the alkyl groups, $C_1$ to $C_4$ alkyl groups, for example, methyl, ethyl or propyl; as the haloalkyl groups, $C_1$ to $C_4$ haloalkyl groups, for example, trifluoromethyl; as the alkoxy groups, $C_1$ to $C_4$ alkoxy groups, for example, methoxy or ethoxy; as the haloalkoxy groups, $C_1$ to $C_4$ haloalkoxy groups, for example, trifluoromethoxy or difluoromethoxy; as the alkylthio groups, $C_1$ to $C_4$ alkylthio groups, for example, methylthio or ethylthio; as the haloalkylthio groups, $C_1$ to $C_4$ haloalkylthio groups, for example, trifluoromethylthio; and as the dialkylamino groups, di($C_1$ to $C_4$ alkyl)amino groups, for example, dimethylamino or diethylamino.

As the substituents A, there may be respectively exemplified: as alkyl groups, usually $C_1$ to $C_{10}$ alkyl groups; as alkenyl groups, usually $C_3$ to $C_{10}$ alkenyl groups; as alkynyl groups, usually $C_3$ to $C_{10}$ alkynyl groups; as cycloalkyl groups, usually $C_3$ to $C_{12}$ cycloalkyl groups; as cycloalkylalkyl groups, usually ($C_3$ to $C_{12}$ cycloalkyl) ($C_1$ to $C_5$ alkyl) groups; a phenyl group; and as phenylalkyl groups, phenyl $C_1$ to $C_5$ alkyl groups.

As the preferred substituents A, there may be respectively exemplified: as the alkyl groups, $C_1$ to $C_8$ alkyl groups, for example, methyl, ethyl, propyl, butyl or pentyl; as the alkenyl groups, $C_3$ to $C_6$ alkenyl groups, for example, 2-propenyl; as the alkynyl groups, $C_3$ to $C_6$ alkynyl groups, for example, 2-propynyl; as the cycloalkyl groups, $C_3$ to $C_6$ cycloalkyl groups, for example, cyclopropyl, cyclobutyl, cyclopentyl or cyclohexyl; as the cycloalkylalkyl groups, ($C_3$ to $C_8$ cycloalkyl) ($C_1$ to $C_3$ alkyl) groups, for example, cyclopropylmethyl or cyclohexylmethyl; a phenyl group; and as the phenylalkyl groups, phenyl $C_1$ to $C_3$ alkyl groups, for example, phenylmethyl or phenylethyl.

As the substituents X, there may be exemplified halogen atoms, usually $C_1$ to $C_6$ alkoxy groups, usually $C_1$ to $C_6$ haloalkoxy groups, usually $C_1$ to $C_6$ alkylthio groups, usually $C_1$ to $C_6$ alkyl groups, usually $C_1$ to $C_6$ haloalkyl groups or usually di($C_1$ to $C_6$ alkyl)amino groups.

As the preferred substituents X, there may be respectively exemplified: as the halogen atoms, fluorine, chlorine or bromine; as the $C_1$ to $C_4$ alkoxy groups, methoxy, ethoxy or propoxy; as the $C_1$ to $C_4$ haloalkoxy groups, trifluoromethoxy, difluoromethoxy or 2,2,2-trifluoroethoxy; as the $C_1$ to $C_4$ alkylthio groups, methylthio or ethylthio; as the $C_1$ to $C_4$ alkyl groups, methyl, ethyl or propyl; as the $C_1$ to $C_4$ haloalkyl groups, trifluoromethyl; and as the di($C_1$ to $C_4$ alkyl)amino groups, dimethylamino or diethylamino.

As the more preferred substituents X, there may be respectively exemplified: as the halogen atoms, fluorine or chlorine; as the $C_1$ to $C_4$ alkoxy groups, methoxy, ethoxy or propoxy; as the $C_1$ to $C_4$ haloalkoxy groups, trifluoromethoxy; as the $C_1$ to $C_4$ alkylthio groups, methylthio or ethylthio; as the $C_1$ to $C_4$ alkyl groups, methyl, ethyl or propyl; and as the $C_1$ to $C_4$ haloalkyl groups, trifluoromethyl.

The integer n represents 0 to an integer selected from numbers of hydrogen atoms which can be substituted with hydrocarbon groups, preferably 0 (indicating unsubstituted condition) to 7. In the case where n is an integer of not less than 2, Xs may be the same or different.

The above-mentioned compound (II) can be readily produced by the method described hereinafter.

Further, as the substituted isocyanate or isothiocyanate (III) in the present invention, there may be used commercially available products or those produced in the following manner.

For example, there may be used substituted isocyanates which can be produced by reacting a primary amine with phosgene or oxalyl dichloride, or substituted thioisocyanates which can be produced by reacting the primary amine with thiophosgene or carbon disulfide. Examples of the primary amines may include alkyl amines such as methyl amine or ethyl amine; alkenyl amines such as allyl amine; alkynyl amines such as propargyl amine; cycloalkyl amines such as cyclopropyl amine, cyclobutyl amine or cyclohexyl amine; haloalkyl amines such as 2,2,2-trifluoroethyl amine, 2,2,3,3,3-pentafluoropropyl amine, 2-chloroethyl amine, 2-bromoethyl amine or 3-chloropropyl amine; alkoxyalkyl amines such as 2-(ethoxy)ethyl amine or 3-(methoxy)propyl amine; alkylthioalkyl amines such as 2-(ethylthio)ethyl amine or 3-(methylthio)propyl amine; aniline; halogen-substituted anilines such as 2-chloroaniline or 4-bromoaniline; alkyl-substituted anilines such as 4-methyl aniline or 4-ethyl aniline; alkoxy-substituted anilines such as 4-methoxy aniline or 3-ethoxy aniline; alkylthio-substituted anilines such as 4-(methylthio) aniline or 3-(methylthio) aniline; haloalkyl-substituted anilines such as 3-(trifluoromethyl) aniline or 4-(trifluoromethyl) aniline; haloalkoxy-substituted anilines such as 3-(trifluoromethoxy) aniline or 4-(trifluoromethoxy) aniline; phenylalkyl amines such as benzyl amine; or the like.

In addition, there may be used substituted isocyanates which can be produced by reacting halides (for example, alkyl halides such as methyl iodide or propyl iodide; alkenyl halides such as allyl iodide or 2-(methyl)allyl chloride; alkynyl halides such as propargyl bromide; alkoxyalkyl halides such as 2-(ethoxy)ethyl chloride; alkylthioalkyl halides such as (methylthio)methyl chloride; or the like) with cyanates, or substituted thioisocyanates which can be produced by the reaction between the halides and thiocyanates, or the like.

Examples of the substituted isocyanates or thioisocyanates are enumerated in Table 1 below.

TABLE 1

(1/2)

phenyl isocyanate; phenyl isothiocyanate; benzyl isocyanate; cyclohexyl isocyanate; 4-chlorophenyl isocyanate; 3-chlorophenyl isocyanate; 2-chlorophenyl isocyanate; 4-methylphenyl isocyanate; 3-methylphenyl isocyanate; 2-methylphenyl isocyanate; 4-methoxyphenyl isocyanate; 2-ethoxyphenyl isocyanate; 4-ethoxyphenyl isocyanate; 4-bromophenyl isocyanate; 4-(methylthio)phenyl isocyanate; 3-(trifluoromethyl)phenyl isocyanate; 4-fluorophenyl isocyanate; 3-fluorophenyl isocyanate; 2-fluorophenyl isocyanate; 2,4-difluorophenyl isocyanate; allyl isocyanate (2/2)

methyl isocyanate; ethyl isothiocyanate; 2-chloroethyl isocyanate; n-propyl isocyanate; n-propyl isothiocyanate; i-propyl isocyanate; t-butyl isocyanate; n-butyl isocyanate; n-butyl isothiocyanate In the addition reaction for producing the present compound (I), the amount of the compound (III) used is usually 0.5 to 5.0 moles, preferably 1.0 to 2.5 moles based on one mole of the compound (II). The reaction temperature is usually −100 to 150° C., preferably −80 to 80° C.

The solvents used in the above addition reaction are those preferable for carrying out the reaction of isocyanate. As such solvents, there may be usually exemplified aliphatic hydrocarbons such as petroleum ethers, pentane, hexane, heptane or methylcyclohexane; ethers such as diethyl ether, dimethoxy ethane, diisopropyl ether, tetrahydrofuran, diethylene glycol dimethyl ether or dioxane; or aromatic hydrocarbons such as benzene, toluene, xylene or methylnaphthalene. These solvents may be used in the form of a mixture of any two or more thereof.

As the acids used in the above-mentioned substitution of the metal with proton, there may be usually exemplified inorganic acids such as hydrochloric acid, hydrobromic acid, hydroiodic acid, perchloric acid or sulfuric acid; organic acids such as formic acid, acetic acid, butyric acid or p-toluene sulfonic acid; or the like. These acids may be used in the form of a mixture of any two or more thereof.

The present compound (I) obtained in the above-mentioned reaction may be separated by ordinary separation methods. For example, the reaction mixture is extracted with an organic solvent, and the solvent is distilled off to obtain a residue. The obtained residue is separated into fractions by column chromatography, and the resultant separated solution is concentrated and treated with poor solvent such as hexane to obtain a precipitate. If required, the precipitate may be further purified by recrystallization.

As the solvents used in the above separation process, there may be usually exemplified aromatic hydrocarbons such as benzene, toluene, xylene or methylnaphthalene; aliphatic hydrocarbons such as petroleum ethers, pentane, hexane, heptane or methylcyclohexane; halogenated hydrocarbons such as methylene chloride, chloroform, carbon tetrachloride or chlorobenzene; amides such as dimethyl formamide, dimethyl acetamide or N-methyl-2-pyrrolidinone; ethers such as diethyl ether, dimethoxy ethane, diisopropyl ether, tetrahydrofuran, diethylene glycol dimethyl ether or dioxane; or the like. As other usable solvents, there may be exemplified water, carbon disulfide, acetonitrile, ethyl acetate, dimethyl sulfoxide, hexamethylphosphoric triamide or the like. These solvents can be used in the form of a mixture of any two or more thereof.

The above-mentioned compound (II) may be produced by metalation of the compound (IV), as shown in the following reaction formula. As metallizing reagents for carrying out the metalation, there may be used those preferable for the metalation. As such metallizing reagents, there may be usually exemplified organic alkali metal compounds such as butyl lithium, sec-butyl lithium, tert-butyl lithium, methyl lithium or phenyl lithium; alkali metal amides such as lithium diisopropyl amide; alkali metals such as lithium, sodium or potassium; alkali earth metals such as magnesium; copper alkali metal; copper alkali earth metal halogen; or the like.

As the pyridine metal compound (II), there may be used, for example, a copper-containing compound (corresponding to the compound (II) wherein M is ½(Cu-alkali metal) or ½(Cu-alkali earth metal halogen)) prepared by reacting a compound of alkali metal such as lithium, sodium or potassium, preferably lithium (corresponding to the compound (II) wherein M is alkali metal, preferably lithium) or a Grignard reagent-type compound (corresponding to the compound (II) wherein M is alkali earth metal halogen) with a monovalent-copper salt such as copper iodide (CuI). This reaction is shown by the following reaction formula (2).

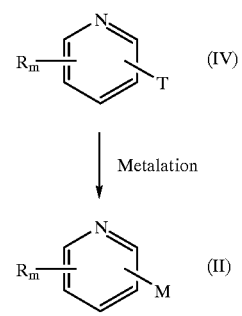

wherein R, M and m are the same as defined hereinbefore with respect to the reaction formula (1), and T represents an atom to be substituted, a halogen atom or a hydrogen atom, which may be bonded to any position of pyridine ring.

The amount of the metallizing reagent used is usually 0.5 to 5.0 moles, preferably 0.8 to 2.0 moles based on one mole of the compound (IV). The reaction temperature is usually −100° C. to 150° C., preferably −80° C. to 80° C.

The solvents used in the above-mentioned reaction may include those preferable for the production of organic metal compounds. As such solvents, there may be usually exemplified aliphatic hydrocarbons such as petroleum ethers, pentane, hexane, heptane or methylcyclohexane; ethers such as diethyl ether, dimethoxy ethane, diisopropyl ether, tetrahydrofuran, diethylene glycol dimethyl ether or dioxane; aromatic hydrocarbons such as benzene, toluene, xylene or methylnaphthalene; or the like. These solvents can be used in the form of a mixture of any two or more thereof.

The thus obtained reaction solution was subjected to the next addition reaction usually without separation of the compound (II). Therefore, the solvent used in the metalation can be used as a solvent for the next addition reaction as it is.

At this time, for example, when M is lithium, different kinds of pyridine metal compounds (II) which are metallized at different positions of the pyridine ring, can be produced by selectively using the compound (IV) to be metalated and the metallizing reagent. Some examples are described below.

In the case of monohalogenopyridine compounds:

When 2-bromopyridine is treated with LDA (lithium diisopropyl amide) in THF (tetrahydrofuran) at −78° C., the hydrogen atom bonded to the 3-position of the pyridine ring is substituted with lithium. On the other hand, when 2-bromopyridine is treated with n-butyl lithium, the bromine atom bonded to the 2-position thereof is substituted with lithium (refer to "Synthesis", 235, 237 (1982)).

When 2-fluoropyridine is treated with LDA in THF at −70° C., the hydrogen atom bonded to the 3-position of the pyridine ring is substituted with lithium (refer to "J. Org. Chem.", 47, 2633 (1982)). On the other hand, when 2-fluoropyridine is treated with n-butyl lithium, an addition reaction product thereof is obtained (refer to "Tetrahedron", 39, 2009 (1983)).

When 3-fluoropyridine is treated with n-butyl lithium in THF and TMEDA (tetramethyl ethylenediamine) at −40° C., the hydrogen atom bonded to the 4-position of the pyridine ring is substituted. On the other hand, when diethyl ether is used instead of THF, the hydrogen atom bonded to the 2-position thereof is substituted (refer to "Tetrahedron", 39, 2009 (1983)).

When 3-chloropyridine is treated with LDA in THF at −60° C., the hydrogen atom bonded to the 4-position of the pyridine ring is substituted (refer to "J. Org. Chem.", 47, 2633 (1982)).

When 4-chloropyridine is treated with LDA in THF at −40° C., the hydrogen atom bonded to the 3-position of the pyridine ring is substituted with lithium (refer to "J. Org. Chem.", 47, 2633(1982)).

In the case of dihalogenopyridines:

When 2,4-dibromopyridine is treated with n-butyl lithium in THF, the bromine atom bonded to the 4-position of the pyridine ring is substituted with lithium (refer to "Thesis, Univ. Antwerp." (1988)).

When 2,5-dibromopyridine is treated with n-butyl lithium in THF, the bromine atom bonded to the 5-position of the pyridine ring is substituted with lithium (refer to "Thesis, Univ. Antwerp." (1988)).

When 2,6-dibromopyridine is treated with n-butyl lithium in diethyl ether, one of the bromine atoms is substituted with lithium (refer to "Chem. Pharm. Bull.", 36, 634 (1988)).

When 3,5-dibromopyridine is treated with n-butyl lithium in diethyl ether, one of the bromine atoms is substituted with lithium (refer to "J. Org. Chem.", 16, 1485 (1988)).

In the case of alkoxypyridines:

When 2-methoxypyridine is treated with LDA, the hydrogen atom bonded to the 3-position of the pyridine ring is substituted with lithium (refer to "J. Org. Chem.", 53, 1367 (1988)).

When 3-ethoxypyridine is treated with n-butyl lithium in diethyl ether and TMEDA, the hydrogen atom bonded to the 4-position of the pyridine ring is substituted with lithium (refer to "Synthesis", 235, 237 (1982)).

Thus, when the compound (IV) is treated under the above-mentioned various production conditions for selective lithium-substitution (lithiation), it is possible to produce such a compound which is substituted with lithium (lithiated) at a required position of the pyridine ring (i.e., compound (II) wherein M is lithium). Accordingly, when the compound (II) wherein M is lithium, is reacted with the compound (III), it is possible to produce the compound (I) to which an N-substituted carbamoyl group or an N-substituted thiocarbamoyl group is bonded at a required position of pyridine ring thereof.

The compound (II) wherein M is magnesium, may be produced by converting the halogen atom bonded to the pyridine ring of the compound (IV) to a Grignard reagent.

The organic copper compound may be produced by the metal-metal exchange reaction between the above-produced organic lithium compound or organic magnesium compound in which lithium or magnesium is bonded to the pyridine ring thereof, and a copper salt.

Further, the compound (IV) used in the process according to the present invention may be produced in the following manner.

First, in the case of halogen-substituted pyridines, as the preferred halogen atoms, there may be exemplified a fluorine atom, a chlorine atom, a bromine atom or an iodine atom. Among these compounds, for example, as monohalogenopyridines (2-fluoropyridine, 3-fluoropyridine, 2-chloropyridine, 3-chloropyridine, 4-chloropyridine, 2-bromopyridine, 3-bromopyridine, 4-bromopyridine, 2-chloro-6-trifluoromethyl pyridine, 6-chloro-2-picoline or the like), and dihalogenopyridines (2,3-dichloropyridine, 2,5-dichloropyridine, 2,6-dichloropyridine, 3,5-dichloropyridine, 2,5-dibromopyridine, 2,6-dibromopyridine, 3,5-dibromopyridine, 2,6-dichloro-3-nitropyridine, 2,6-dichloro-3-trifluoromethyl pyridine, 2,6-dichloro-4-trifluoromethyl pyridine or the like), there may be used commercially available products. In addition, 2,6-dibromo-4-methyl pyridine can be produced by substituting a hydroxyl group of 2-bromo-6-hydroxy-4-methyl pyridine with a halogen atom, as described in Japanese Patent Application Laid-open (KOKAI) No. 6-40813. Also, for example, 2-bromo-4-methyl pyridine or 2-bromo-6-methyl pyridine can be produced by substituting a hydroxyl group of 2-hydroxy-4-methyl pyridine or 2-hydroxy-6-methyl pyridine with a halogen atom. Further, among these compounds, with respect to such compounds having a halogen atom bonded to the 2- or 4-position of the pyridine ring, by subjecting (substituted or unsubstituted) alcohols, (substituted or unsubstituted) alkylthiols, (substituted or unsubstituted) alkylamines, di(substituted or unsubstituted) alkylamines, (substituted or unsubstituted) phenols, (substituted or unsubstituted) thiophenols, (substituted or unsubstituted) aniline, di(substituted or unsubstituted) phenyl amines or (substituted or unsubstituted)phenylalkyl amines, to nucleophilic halogen-substitution reaction under basic conditions, there may be produced corresponding halogen-substituted alkoxy compounds, alkylthio compounds, alkylamino compounds, dialkylamino compounds, (substituted or unsubstituted)phenoxy compounds, (substituted or unsubstituted)phenylthio compounds, (substituted or unsubstituted)phenylamino compounds, di(substituted or unsubstituted)phenylamino compounds or (substituted or unsubstituted) phenylalkylamino compounds. Also, with respect to such compounds having a nitro group bonded to the 2- or 4-position of the pyridine ring (among them, for example, 2-nitropyridine has been described in "Ber.", 64, 767 (1931); and 2,6-dichloro-4-nitropyridine has been described in Japanese Patent Application Laid-open (KOKAI) No. 57-126474 (1982) in which the production of 2,6-dibromo-4-nitropyridine or the like have also been described), by subjecting (substituted or unsubstituted) alcohols, (substituted or unsubstituted) alkylthiols, (substituted or unsubstituted)alkyl amines, di(substituted or unsubstituted) alkyl amines, (substituted or unsubstituted) phenols, (substituted or unsubstituted) thiophenols, (substituted or unsubstituted) anilines, di(substituted or unsubstituted) phenyl amines or (substituted or unsubstituted)phenylalkyl amines, to nucleophilic nitro-substitution reaction under basic conditions, there may be produced corresponding nitro-substituted (substituted or unsubstituted)alkoxy compounds, (substituted or unsubstituted)alkylthio compounds, (substituted or unsubstituted)alkylamino compounds, di(substituted or unsubstituted)alkylamino compounds, (substituted or unsubstituted) phenoxy compounds, (substituted or unsubstituted)phenylthio compounds, (substituted or unsubstituted)phenylamino compounds, di(substituted or unsubstituted)phenylamino compounds or (substituted or unsubstituted) phenylalkylamino compounds. Furthermore, by conducting nucleophilic substitution reaction between compounds having a hydroxyl group, a thiol group or an amino group on the pyridine ring thereof, such as pyridinol compounds (including commercially available products such as 2-pyridinol, 3-pyridinol, 4-pyridinol, 2-bromo-3-pyridinol, 5-chloro-2-pyridinol, 2-chloro-3-pyridinol, 5-chloro-2-pyridinol, 6-chloro-2-pyridinol or the like, or those produced by hydrolysis of nitro compounds, hydrolysis of halogen compounds, diazotation of amino compounds followed by hydrolysis thereof, or the like), pyridine thiol compounds (which can be produced by thiol-substitution of nitro compounds or halogen compounds, or the like) or aminopyridine compounds (including commercially available products such as 2-aminopyridine, 3-aminopyridine or 4-aminopyridine, or those produced by reduction of nitro compounds such as 2-chloro-3-nitropyridine or 2,6-dichloro-3-nitropyridine or by the substitution reaction between the above-mentioned halogen atoms or nitrocompounds and amino compounds, or the like), and (substituted or unsubstituted)alkyl halides or (substituted or unsubstituted)phenylalkyl halides under basic conditions, there may be produced corresponding (substituted or unsubstituted)alkoxy compounds, (substituted or unsubstituted)alkylthio compounds, (substituted or unsubstituted)alkylamino compounds, di(substituted or unsubstituted)alkylamino compounds, (substituted or unsubstituted)alkyl{(substituted or unsubstituted) phenyl}amino compounds, (substituted or unsubstituted) alkyl{(substituted or unsubstituted) phenylalkyl}amino compounds or {(substituted or unsubstituted)phenyl}{(substituted or unsubstituted) phenylalkyl}amino compounds.

The process for the production of such compounds (IV) having substituent groups on the 2-, 4- and 6-positions of the pyridine ring thereof, is shown by the following reaction formula (3).

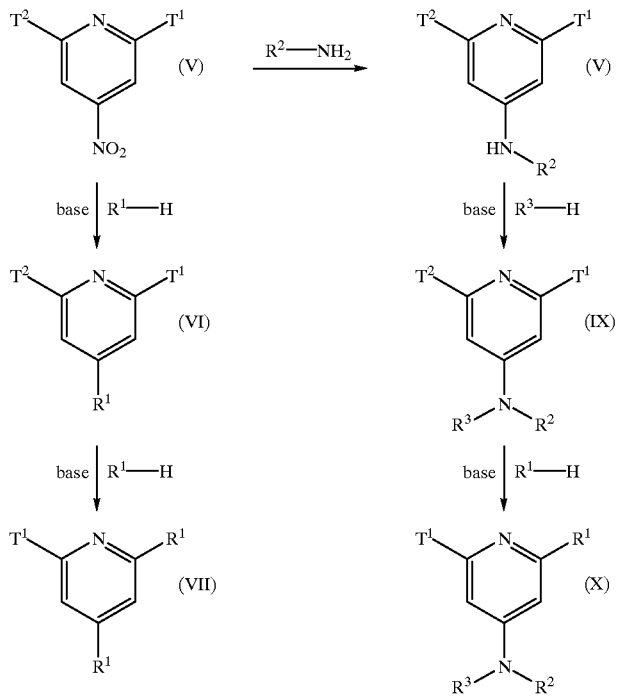

wherein $R^1$ is an alkoxy group, an alkylthio group or a (substituted or unsubstituted)phenoxy group, and $R^1$s may be the same or different; $R^2$ is an alkyl group; $R^3$ is an alkyl group or a phenylalkyl group; $T^1$, $T^2$ and $T^3$ are a halogen atom and may be the same or different in which the halogen atom represents a fluorine atom, a chlorine atom, a bromine atom or an iodine atom.

As shown in the reaction formula (3), the compound (VIII) can be produced by nucleophilically substituting the nitro group of the compound (V) with $R^2-NH_2$ {(substituted or unsubstituted)alkyl amine} under basic conditions (in the case of alkylamine or the like, the use of base is occasionally unnecessary since these compounds themselves exhibit a high nucleophilic property).

The compound (IX) can be produced by subjecting the compound (VIII) and $R^3-X$ {alkyl halide or (substituted or unsubstituted)phenylalkyl halide} to nucleophilic substitution reaction under basic conditions.

The compounds (VI), (VII) and (X) can be produced by subjecting the compound (V) or the compound (IX) and $R^1-H$ (alkanol, alkylthiol or (substituted or unsubstituted) phenol) to nucleophilic substitution reaction under basic conditions.

As these alkyl halides, (substituted or unsubstituted) phenylalkyl halides, alkanols, alkylthiols, alkylamines or (substituted or unsubstituted) phenols, there may be used commercially available products or those produced by known techniques. For example, as the (substituted or unsubstituted) phenols, the following compounds may be exemplified:

Phenol;

Halogen-substituted phenols such as 2-chlorophenol, 3-chlorophenol or 4-chlorophenol;

Alkyl-substituted phenols such as 3-methylphenol;

Alkoxy-substituted phenols such as 3-methoxyphenol;

Alkylthio-substituted phenols such as 3-(methylthio) phenol;

Haloalkyl-substituted phenols such as 3-(trifluoromethyl) phenol;

Haloalkoxy-substituted phenols such as 3-(trifluoromethoxy)phenol or 3-(difluoromethoxy) phenol;

Haloalkylthio-substituted phenols such as 3-(trifluoromethylthio)phenol; or

Dialkylamino-substituted phenols such as 3-(dimethylamino)phenol.

Thus, the process for producing N-substituted pyridine carboxamide or thiocarboxamide according to the present invention can be applied to even such compounds having an oxidation-susceptible substituent group. Further, in the production process according to the present invention, N-substituted pyridine thiocarboxamide can be produced without sulfidization of corresponding N-substituted pyridine carboxamide. Accordingly, the process of the present invention is industrially useful.

BEST MODE FOR CARRYING OUT THE INVENTION

The present invention is described in more detail below by examples, but these examples are not intended to limit the scope of the present invention.

Production Example 1

Production of N-(i-propyl)-4-pyridine carboxamide (compound No. I-1)

1.0 g (0.0051 mol) of 4-bromopyridine hydrochloride was suspended in about 30 ml of diethyl ether. While cooling the suspension in a dry ice-acetone bath in an argon atmosphere, 6.6 ml of about 1.65M hexane solution of n-butyl lithium (hereinafter referred to merely as "BuLi") (0.0051×2.1 mol) was added to the suspension, followed by stirring for about 10 minutes. After 1.13 g (0.0067×2.0 mol) of isopropyl isocyanate dissolved in about 10 ml of diethyl ether was added to the reaction solution, the bath was removed and stirred at room temperature for about one hour. The reaction solution was mixed with about 10 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.23 g; yield by percentage: 27%; solid; melting point: 105 to 107° C.; $^1$H-NMR (60 MHz, CDCl$_3$, δ): 1.23 (6H, d, J=6.4 Hz), 3.7–4.6 (1H, mult.), 6.7–7.4 (1H, br), 7.4–7.8 (2H, complex), 8.4–8.8 (2H, complex).

Production Example 2

Production of N-(i-propyl)-4-methyl-2-pyridine carboxamide (compound No. I-3)

(1) Production of 2-bromo-4-methyl pyridine as an intermediate product 4.93 g (0.045 mol) of 2-hydroxy-4-methyl pyridine was mixed with 50 ml of bromoform and then with 14.2 g (0.045×1.2 mol) of phosphorus tribromide, followed by treating the mixture under reflux for about 3 hours. The obtained reaction solution was concentrated and then mixed with water. After stirring for a while, the reaction solution was distributed with ethyl acetate-water, followed by washing with saturated sodium bicarbonate water and saturated brine. The organic phase of the obtained solution was dried with anhydrous sodium sulfate. The resultant solution was concentrated and then purified by silica gel column chromatography (eluting solution: ethyl acetate/hexane), thereby obtaining an aimed product.

Yield by weight: 1.17 g; yield by percentage: 15%; oily substance; $^1$H-NMR (60 MHz, CDCl$_3$, δ): 2.27 (3H, s), 7.00 (1H, d, J=6 Hz), 7.23 (1H, s), 8.17 (1H, d, J=6 Hz).

(2) Production of N-(i-propyl)-4-methyl-2-pyridine carboxamide (compound No. I-3)

1.0 g (0.0058 mol) of 2-bromo-4-methyl pyridine was dissolved in about 30 ml of diethyl ether. While cooling the solution in a dry ice-acetone bath in an argon atmosphere, 3.9 ml of about 1.65M hexane solution of BuLi (0.0058×1.1 mol) was added to the solution, followed by stirring the mixture for about 10 minutes. After 1.0 g (0.0058×2.0 mol) of isopropyl isocyanate dissolved in about 10 ml of diethyl ether was added to the reaction solution, the bath was removed and stirred at room temperature for about one hour. The reaction solution was mixed with about 10 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.78 g; yield by percentage: 82%; oily substance; $^1$H-NMR (60 MHz, CDCl$_3$, δ): 1.25 (6H, d, J=6.4 Hz), 2.36 (3H, s), 3.7–4.6 (1H, mult.), 7.14 (1H, d, J=6 Hz), 7.5–8.2 (1H, br), 7.94 (1H, s), 8.31 (1H, d, J=6 Hz).

Production Example 3

Production of N-(i-propyl)-4-chloro-3-pyridine carboxamide (compound No. I-4)

1.0 g (0.0067 mol) of 4-chloropyridine hydrochloride was suspended in about 30 ml of tetrahydrofuran. While cooling the suspension in a dry ice-acetone bath in an argon atmosphere, 7.0 ml of about 2.0M heptane/tetrahydrofuran/ethyl benzene solution of lithium diisopropyl amide (0.0067×2.1 mol) was added to the suspension, followed by stirring for about 10 minutes. After 1.13 g (0.0067×2.0 mol) of isopropyl isocyanate dissolved in about 10 ml of tetrahydrofuran was added to the reaction solution, the solution was removed from the bath and stirred at room temperature for about one hour. The reaction solution was mixed with about 10 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.52 g; yield by percentage: 39%; solid; melting point: 96 to 98° C.; $^1$H-NMR (60 MHz, CDCl$_3$, δ): 1.17 (6H, d, J=7 Hz), 4.14 (1H, oct., J=7 Hz), 6.4–7.1 (1H, br), 7.18 (1H, d, J=5.6 Hz), 8.31 (1H, d, J=5.6 Hz), 8.49 (1H, s).

Production Example 4
Production of N-(4-methylphenyl)-6-bromo-4-methoxy-2-pyridine carboxamide (compound No. I-7)
(1) Production of 2,6-dibromo-4-methoxy pyridine as an intermediate product 1.49 g (ca. 60% in mineral oil; 0.0355×1.05 mol) of sodium hydride was washed with hexane and suspended in tetrahydrofuran. The suspension was mixed with 1.70 g (0.0355×1.5 mol) of methanol and then with 10.00 g (0.0355 mol) of 2,6-dibromo-4-nitropyridine, and stirred at room temperature for about one hour. Further, the suspension was mixed with 0.2 g (ca. 60% in mineral oil; 0.0355×0.14 mol) of sodium hydride, and stirred for about one hour. Next, 1.0 g (0.0355×0.9 mol) of methanol was added to the suspension, and after it was determined that no foaming was caused therein, the reaction solution was distributed with ethyl acetate-saturated sodium bicarbonate water. The organic phase of the obtained reaction solution was washed with saturated brine, dried with anhydrous sodium sulfate and then concentrated, thereby obtaining an aimed product.

Yield by weight: 9.27 g; yield by percentage: 98%; solid; melting point: 131 to 133° C.; $^1$H-NMR (60 MHz, CDCl$_3$, δ): 3.79 (3H, s), 6.89 (2H, s).

(2) Production of N-(4-methylphenyl)-6-bromo-4-methoxy-2-pyridine carboxamide (compound No. I-7)

2.0 g (0.0075 mol) of 2,6-dibromo-4-methoxy pyridine was added to about 30 ml of diethyl ether. While cooling the obtained solution in a dry ice-acetone bath in an argon atmosphere, the solution was mixed with 6.0 ml of about 1.6M hexane solution of BuLi (0.0075×1.3 mol), followed by stirring for about 10 minutes. After 2.0 g (0.0075×2.0 mol) of 4-methylphenyl isocyanate dissolved in about 5 ml of diethyl ether was added to the reaction solution, the bath was removed and stirred at room temperature for about 40 minutes. The reaction solution was mixed with about 10 ml of 1.2N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 1.38 g; yield by percentage: 57%; solid; melting point: 153 to 157° C.; $^1$H-NMR (60 MHz, CDCl$_3$, δ): 2.28 (3H, s), 3.82 (3H, s), 7.02 (1H, d, J=2 Hz), 7.09 (2H, d, J=8 Hz), 7.56 (2H, d, J=8 Hz), 7.68 (1H, d, J=2 Hz), 9.53 (1H, s).

Production Example 5
Production of N-benzyl-6-bromo-4-methoxy-2-pyridine carboxamide (compound No. I-9)

1.0 g (0.0037 mol) of 2,6-dibromo-4-methoxy pyridine was suspended in about 15 ml of diethyl ether. While cooling the suspension in a dry ice-acetone bath in an argon atmosphere, 2.6 ml of about 1.6M hexane solution of BuLi (0.0037×1.1 mol) was added to the suspension, followed by stirring for about 10 minutes. After 0.75 g (0.0037×1.5 mol) of benzyl isocyanate dissolved in about 5 ml of diethyl ether was added to the reaction solution, the bath was removed and stirred at room temperature for about 40 minutes. The reaction solution was mixed with about 5 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 1.04 g; yield by percentage: 86%; solid; melting point: 107 to 111° C.; $^1$H-NMR (60 MHz, CDCl$_3$, δ): 3.75 (3H, s), 4.52 (2H, d, J=6 Hz), 6.94 (1H, d, J=2 Hz), 7.20 (5H, s), 7.59 (1H, d, J=2 Hz), 7.8–8.4 (1H, br).

Production Example 6
Production of N-(i-propyl)-6-bromo-4-methoxy-2-pyridine carboxamide (compound No. I-10)

1.0 g (0.0037 mol) of 2,6-dibromo-4-methoxy pyridine was suspended in about 15 ml of diethyl ether. While cooling the suspension in a dry ice-acetone bath in an argon atmosphere, 2.6 ml of about 1.6M hexane solution of BuLi (0.0037×1.1 mol) was added to the suspension, followed by stirring for about 10 minutes. After 0.64 g (0.0037×2.0 mol) of i-propyl isocyanate dissolved in about 5 ml of diethyl ether was added to the reaction solution, the bath was removed and stirred at room temperature for about 40 minutes. The reaction solution was mixed with about 5 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.76 g; yield by percentage: 74%; solid; melting point: 70 to 76° C.; $^1$H-NMR (60 MHz, CDCl$_3$, δ): 1.25 (6H, d, J=6.4 Hz), 3.82 (3H, s), 3.8–4.6 (1H, mult.), 6.98 (1H, d, J=2 Hz), 7.0–7.9 (1H, br), 7.61 (1H, d, J=2 Hz).

Production Example 7
Production of N-phenyl-4-methoxy-6-{3-(trifluoromethyl)phenoxy}-2-pyridine carboxamide (compound No. I-14)
(1) Production of 2-bromo-4-methoxy-6-{3-(trifluoromethyl)phenoxy} pyridine as an intermediate product 3.34 g (0.187×1.1 mol) of 3-(trifluoromethyl) phenol was dissolved in about 30 ml of dimethyl formamide. The solution was further mixed with 0.78 g (ca. 60% in mineral oil; 0.0187×1.04 mol) of sodium hydride and then with 5.00 g (0.0187 mol) of 2,6-dibromo-4-methoxy pyridine. After stirring at about 120° C. for about 2 hours, the mixture was allowed to stand for cooling to room temperature. After the reaction solution was distributed with hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained product was subjected to recrystallization using hexane, thereby obtaining an aimed product.

Yield by weight: 3.23 g; yield by percentage: 50%; solid; melting point: 57 to 60° C.; $^1$H-NMR (60 MHz, CDCl$_3$, δ): 3.75 (3H, s), 6.26 (1H, d, J=2 Hz), 6.75 (1H, d, J=2 Hz), 7.0–7.6 (4H, complex).

(2) Production of N-phenyl-4-methoxy-6-{3-(trifluoromethyl)phenoxy}-2-pyridine carboxamide (compound No. I-14)

1.0 g (0.0029 mol) of 2-bromo-4-methoxy-6-{3-(trifluoromethyl)phenoxy} pyridine was dissolved in about 15 ml of diethyl ether. While cooling the solution in a dry ice-acetone bath in an argon atmosphere, the solution was mixed with 1.9 ml of about 1.69M hexane solution of BuLi (0.0029×1.1 mol), followed by stirring for about 10 minutes. After 0.86 g (0.0029×2.5 mol) of phenyl isocyanate dissolved in about 5 ml of diethyl ether was added to the reaction solution, the bath was removed and stirred at room temperature for about 30 minutes. The reaction solution was mixed with about 5 ml of 1.2N hydrochloric acid aqueous solution, and then distributed with ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 0.57 g; yield by percentage: 51%; solid; melting point: 140 to 142° C.; $^1$H-NMR (60 MHz, CDCl$_3$, δ): 3.83 (3H, s), 6.48 (1H, d, J=2 Hz), 6.8–7.7 (9H, complex), 7.52 (1H, d, J=2 Hz), 9.23 (1H, s).

Production Example 8
Production of N-phenyl-4-methoxy-6-{3-(trifluoromethoxy)-phenoxy)}-2-pyridine carboxamide (compound No. I-23)
(1) Production of 2-bromo-4-methoxy-6-{3-(trifluoromethoxy)phenoxy} pyridine as an intermediate product 2.00 g (0.00937×1.2 mol) of 3-(trifluoromethoxy) phenol was dissolved in about 20 ml of dimethyl formamide. The solution was further mixed with 0.39 g (ca. 60% in mineral oil; 0.00937×1.04 mol) of sodium hydride and then with 2.50 g (0.00937 mol) of 2,6-dibromo-4-methoxy pyridine. After stirring at about 110° C. for about 4 hours, the mixture was allowed to stand for cooling to room temperature. After the reaction solution was distributed with hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained product was subjected to recrystallization using hexane, thereby obtaining an aimed product.

Yield by weight: 1.40 g; yield by percentage: 41%; oily substance; $^1$H-NMR (60 MHz, CDCl$_3$, δ): 3.73 (3H, s), 6.25 (1H, d, J=2 Hz), 6.69 (1H, d, J=2 Hz), 6.7–7.5 (4H, complex).
(2) Production of N-phenyl-4-methoxy-6-{3-(trifluoromethoxy)phenoxy}-2-pyridine carboxamide (compound No. I-23)

1.0 g (0.0027 mol) of 2-bromo-4-methoxy-6-{3-(trifluoromethoxy)phenoxy} pyridine was dissolved in about 15 ml of diethyl ether. While cooling the solution in a dry ice-acetone bath in an argon atmosphere, the solution was mixed with 2.6 ml of about 1.6M hexane solution of BuLi (0.0027×1.5 mol), followed by stirring for about 10 minutes. After 0.74 g (0.0027×2.3 mol) of phenyl isocyanate dissolved in about 5 ml of diethyl ether was added to the reaction solution, the bath was removed and stirred at room temperature for about 45 minutes. The reaction solution was mixed with about 5 ml of 1.2N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 0.74 g; yield by percentage: 67%; solid; melting point: 95 to 98° C.; $^1$H-NMR (60 MHz, CDCl$_3$, δ): 3.82 (3H, s), 6.39 (1H, d, J=2 Hz), 6.6–7.6 (9H, complex), 7.44 (1H, d, J=2 Hz), 9.19 (1H, s).

Production Example 9
Production of N-phenyl-4-methylmercapto-6-{3-(trifluoromethyl)phenoxy}-2-pyridine carboxamide (compound No. I-24)
(1) Production of 2,6-dibromo-4-methylmercapto pyridine as an intermediate product A THF solution containing 3.00 g (0.0106 mol) of 2,6-dibromo-4-nitropyridine was mixed with a 15% aqueous solution containing 5.22 g (0.0106×1.05 mol) of sodium methyl mercaptan, and the mixture was stirred at room temperature for about one hour. Further, the obtained solution was mixed with a 15% aqueous solution containing 0.5 g (0.0106×0.1 mol) of sodium methyl mercaptan and stirred at room temperature for about one hour. After the resultant reaction solution was distributed with ethyl acetate-water, the organic phase of the solution was washed with saturated sodium bicarbonate water and saturated brine, dried with anhydrous sodium sulfate, concentrated and then subjected to precipitation by adding hexane thereto, thereby obtaining an aimed product.

Yield by weight: 2.64 g; yield by percentage: 88%; solid; melting point: 115 to 119° C.; $^1$H-NMR (60 MHz, CDCl$_3$, δ): 2.42 (3H, s), 7.04 (2H, s).
(2) Production of 2-bromo-4-methylmercapto-6-{3-(trifluoromethyl)phenoxy} pyridine as an intermediate product 2.06 g (0.0106×1.2 mol) of 3-(trifluoromethyl) phenol was dissolved in about 20 ml of dimethyl formamide. The solution was further mixed with 0.45 g (ca. 60% in mineral oil; 0.0106×1.06 mol) of sodium hydride and then with 3.00 g (0.0106 mol) of 2,6-dibromo-4-methylmercapto pyridine. After stirring at about 110° C. for about 2 hours, the mixture was allowed to stand for cooling to room temperature. After the reaction solution was distributed with hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained product was subjected to recrystallization using hexane, thereby obtaining an aimed product.

Yield by weight: 2.49 g; yield by percentage: 64%; solid; melting point: 54 to 57° C.; $^1$H-NMR (60 MHz, CDCl$_3$, δ): 2.37 (3H, s), 6.50 (1H, d, J=2 Hz), 6.89 (1H, d, J=2 Hz), 7.0–7.5 (4H, complex).
(3) Production of N-phenyl-4-methylmercapto-6-{3-(trifluoromethyl)phenoxy}-2-pyridine carboxamide (compound No. I-24)

0.8 g (0.0022 mol) of 2-bromo-4-methylmercapto-6-{3-(trifluoromethyl)phenoxy} pyridine was dissolved in about 15 ml of diethyl ether. While cooling the solution in a dry ice-acetone bath in an argon atmosphere, 1.5 ml of about 1.6M hexane solution of BuLi (0.0022×1.1 mol) was added to the solution, followed by stirring for about 10 minutes. After 0.52 g (0.0022×2.0 mol) of phenyl isocyanate dissolved in about 5 ml of diethyl ether was added to the reaction solution, the bath was removed and stirred at room temperature for about 30 minutes. The reaction solution was mixed with about 5 ml of 1.2N hydrochloric acid aqueous solution, and then distributed with ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 0.52 g; yield by percentage: 59%; solid; melting point: 131 to 133° C.; $^1$H-NMR (60 MHz, CDCl$_3$, δ): 2.44 (3H, s), 6.76 (1H, d, J=2 Hz), 6.8–7.6 (9H, complex), 7.71 (1H, d, J=2 Hz), 9.11 (1H, s).

Production Example 10
Production of N-phenyl-4-dimethylamino-6-{3-(trifluoromethyl)phenoxy}-2-pyridine carboxamide (compound No. I-25)
(1) Production of 2,6-dibromo-4-methylamino pyridine as an intermediate product About 10 ml of an acetonitrile solution containing 1.00 g (0.00355 mol) of 2,6-dibromo-4-nitropyridine was mixed with a 40% aqueous solution containing 1.10 g (0.00355×4.0 mol) of methyl amine, and the mixture was stirred at room temperature for about 2 hours. After the reaction solution was distributed with ethyl acetate-water, the organic phase of the obtained solution was washed with saturated sodium bicarbonate water and saturated brine, dried with anhydrous sodium sulfate, concentrated and then subjected to precipitation by adding hexane thereto, thereby obtaining an aimed product.

Yield by weight: 0.82 g; yield by percentage: 87%; solid; melting point: 189 to 193° C.; $^1$H-NMR (60 MHz, CDCl$_3$+DMSO-d$_6$, δ): 2.70 (3H, d, J=5 Hz), 6.49 (2H, s), 6.4–7.0 (1H, mult.).

(2) Production of 2,6-dibromo-4-dimethylamino pyridine as an intermediate product 2.4 g (0.0090 mol) of 2,6-dibromo-4-methylamino pyridine was added to a mixed solvent containing about 30 ml of dimethyl formamide and about 40 ml of diethyl ether. Further, 0.38 g (ca. 60% in mineral oil; 0.090×1.06 mol) of sodium hydride was added to the solution. The solution was mixed with 1.54 g (0.0090×1.2 mol) of methyl iodide, and stirred at room temperature for about one hour, followed by treating the solution under reflux for about one hour. After the reaction solution was distributed with hexane-sodium bicarbonate water, the organic phase of the solution was washed with saturated brine, dried with anhydrous sodium sulfate, and concentrated. The obtained solid was washed out with hexane, thereby obtaining an aimed product.

Yield by weight: 2.39 g; yield by percentage: 95%; solid; melting point: 141 to 144° C.; $^1$H-NMR (60 MHz, CDCl$_3$, δ): 2.91 (6H, s), 6.43 (2H, s).

(3) Production of 2-bromo-4-dimethylamino-6-{3-(trifluoromethyl)phenoxy} pyridine as an intermediate product 1.4 g (0.0071×1.2 mol) of 3-(trifluoromethyl) phenol was dissolved in about 20 ml of dimethyl formamide. The solution was further mixed with 0.30 g (ca. 60% in mineral oil; 0.0071×1.06 mol) of sodium hydride and then with 2.00 g (0.0071 mol) of 2,6-dibromo-4-dimethylamino pyridine. After treating the solution under reflux for about 6 hours, the solution was allowed to stand for cooling to room temperature. After the reaction solution was distributed with hexane-saturated sodium bicarbonate water, the organic phase of the obtained solution was washed with saturated brine and dried with anhydrous sodium sulfate, followed by concentration thereof. Thereafter, the concentrated solution was purified by silica gel column chromatography (eluting solution: ethyl acetate/hexane) and the obtained product was subjected to recrystallization using hexane, thereby obtaining an aimed product.

Yield by weight: 1.67 g; yield by percentage: 65%; solid; melting point: 61 to 66° C.; $^1$H-NMR (60 MHz, CDCl$_3$, δ): 2.86 (6H, s), 6.88 (1H, d, J=2 Hz), 6.38 (1H, d, J=2 Hz), 6.9–7.5 (4H, complex).

(4) Production of N-phenyl-4-dimethylamino-6-{3-(trifluoromethyl)phenoxy}-2-pyridine carboxamide (compound No. I-25)

0.8 g (0.0022 mol) of 2-bromo-4-dimethylamino-6-{3-(trifluoromethyl)phenoxy} pyridine was dissolved in about 15 ml of diethyl ether. While cooling the solution in a dry ice-acetone bath in an argon atmosphere, 1.5 ml of about 1.6M hexane solution of BuLi (0.0022×1.1 mol) was added to the solution, followed by stirring for about 10 minutes. After 0.60 g (0.0022×2.3 mol) of phenyl isocyanate dissolved in about 5 ml of diethyl ether was added to the reaction solution, the bath was removed and stirred at room temperature for about 30 minutes. The reaction solution was mixed with about 5 ml of 1.2N hydrochloric acid aqueous solution, and then distributed with ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then precipitated with hexane, thereby obtaining an aimed product.

Yield by weight: 0.55 g; yield by percentage: 62%; solid; melting point: 135 to 138° C.; $^1$H-NMR (60 MHz, CDCl$_3$, δ): 2.96 (6H, s), 6.05 (1H, d, J=2 Hz), 6.7–7.6 (10H, complex), 9.33 (1H, s).

Production Example 11
Production of N-phenyl-4-methoxy-6-{3-(trifluoromethyl)phenoxy}-2-pyridine thiocarboxamide (compound No. I-26)

0.8 g (0.0023 mol) of 2-bromo-4-methoxy-6-{3-(trifluoromethyl)phenoxy} pyridine was dissolved in about 15 ml of diethyl ether. While cooling the solution in a dry ice-acetone bath in an argon atmosphere, 1.5 ml of about 1.69M hexane solution of BuLi (0.0023×1.1 mol) was added thereto, followed by stirring the solution for about 10 minutes. After 0.62 g (0.0023×2.0 mol) of phenyl isothiocyanate dissolved in about 5 ml of diethyl ether was added to the reaction solution, the bath was removed and stirred at room temperature for about 30 minutes. The reaction solution was mixed with about 5 ml of 1.2N aqueous hydrochloric acid solution, and then distributed with ethyl acetate-saturated sodium bicarbonate water, followed by washing with saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then precipitated with hexane, thereby obtaining an aimed product.

Yield by weight: 0.53 g; yield by percentage: 57%; solid; melting point: 126 to 128° C.; $^1$H-NMR (60 MHz, CDCl$_3$, δ): 3.79 (3H, s), 6.43 (1H, d, J=2 Hz), 6.8–7.7 (9H, complex), 7.92 (1H, d, J=2 Hz), 11.32 (1H, s).

Production Example 12
Production of N-phenyl-4-{methyl(phenylmethyl)amino}-6-{3-(trifluoromethyl)-phenoxy}-2-pyridine carboxamide (compound No. I-27)
(1) Production of 4-{methyl(phenylmethyl)amino}-2,6-dibromo pyridine as an intermediate product 3.0 g (0.011 mol) of 2,6-dibromo-4-methylamino pyridine was added to a mixed solvent containing about 30 ml of dimethyl formamide and about 50 ml of tetrahydrofuran. The solution was further mixed with 0.47 g (ca. 60% in mineral oil; 0.011×1.07 mol) of sodium hydride. The obtained solution was mixed with 2.32 g (0.011×1.2 mol) of benzyl bromide and stirred at room temperature for about 3 hours. After the reaction solution was distributed with hexane-sodium bicarbonate water, the organic phase of the solution was washed with saturated brine, dried with anhydrous sodium sulfate, and then concentrated. The obtained solid was washed out with hexane, thereby obtaining an aimed product.

Yield by weight: 3.0 g; yield by percentage: 75%; solid; melting point: 125 to 129° C.; $^1$H-NMR (60 MHz, CDCl$_3$, δ): 2.92 (3H, s), 4.45 (2H, s), 6.53 (2H, s), 6.7–7.4 (5H, complex).

(2) Production of 2-bromo-4-{methyl(phenylmethyl) amino}-6-{3-(trifluoromethyl)phenoxy} pyridine as an intermediate product 1.56 g (0.0080×1.2 mol) of 3-(trifluoromethyl) phenol was dissolved in about 20 ml of dimethyl formamide. The solution was further mixed with 0.34 g (ca. 60% in mineral oil; 0.0080×1.06 mol) of sodium hydride and then with 2.85 g (0.0080 mol) of 4-(methyl(phenylmethyl)amino)-2,6-dibromo pyridine. After treating the solution under reflux for about 6 hours, the obtained reaction solution was allowed to stand for cooling to room temperature. After the reaction solution was distributed with hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained eluate was subjected to recrystallization using hexane, thereby obtaining an aimed product.

Yield by weight: 2.15 g; yield by percentage: 61%; solid; melting point: 84 to 87° C.; $^1$H-NMR (60 MHz, CDCl$_3$, δ): 2.92 (3H, s), 4.38 (2H, s), 5.95 (1H, d. J=2 Hz), 6.48 (1H, d, J=2 Hz), 6.7–7.6 (9H, complex).

(3) Production of N-phenyl-4-{methyl(phenylmethyl) amino}-6-{3-(trifluoromethyl)phenoxy}-2-pyridine carboxamide (compound No. I-27)

1.00 g (0.0023 mol) of 2-bromo-4-{methyl (phenylmethyl) amino}-6-{3-(trifluoromethyl)phenoxy} pyridine was dissolved in about 20 ml of diethyl ether. While cooling the solution in a dry ice-acetone bath in an argon atmosphere, 2.2 ml of about I.6M hexane solution of BuLi (0.0023×1.5 mol) was added to the solution, followed by stirring for about 10 minutes. After 0.62 g (0.0023×2.3 mol) of phenyl isocyanate dissolved in about 5 ml of diethyl ether was added to the reaction solution, the bath was removed and stirred at room temperature for about one hour. The reaction solution was mixed with about 5 ml of 1.2N aqueous hydrochloric acid solution, and then distributed with ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 0.50 g; yield by percentage: 47%; solid; melting point: 111 to 114° C.; $^1$H-NMR (60 MHz, CDCl$_3$, δ): 3.03 (3H, s), 4.32 (2H, s), 6.09 (1H, d, J=2 Hz), 6.7–7.6 (15H, complex), 9.28 (1H, s).

Production Example 13

Production of N-(n-propyl)-4-methoxy-6-{3-(trifluoromethyl)phenoxy}-2-pyridine carboxamide (compound No. I-30)

0.8 g (0.0023 mol) of 2-bromo-4-methoxy-6-{3-(trifluoromethyl)phenoxy} pyridine was dissolved in about 15 ml of diethyl ether. While cooling the solution in a dry ice-acetone bath in an argon atmosphere, 1.6 ml of about 1.6M hexane solution of BuLi (0.0023×1.1 mol) was added thereto, followed by stirring for about 10 minutes. After 0.39 g (0.0023×2.0 mol) of n-propyl isocyanate dissolved in about 5 ml of diethyl ether was added to the reaction solution, the bath was removed and stirred at room temperature for about one hour. The reaction solution was mixed with about 5 ml of 1.0N aqueous hydrochloric acid solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.65 g; yield by percentage: 80%; solid; melting point: 60 to 64° C.; $^1$H-NMR (60 MHz, CDCl$_3$, δ): 0.81 (3H, t, J=7 Hz), 1.46 (2H, sext, J=7 Hz), 2.9–3.6 (2H, q, J=6.4 Hz), 3.81 (3H, s), 6.41 (1H, d, J=2 Hz), 7.0–7.8 (6H, complex).

Production Example 14

Production of N-(i-propyl)-4-methylmercapto-6-{3-(trifluoromethyl)phenoxy}-2-pyridine carboxamide (compound No. I-37)

0.75 g (0.0021 mol) of 2-bromo-4-methylmercapto-6-{3-(trifluoromethyl)phenoxy} pyridine was suspended in about 15 ml of diethyl ether. While cooling the suspension in a dry ice-acetone bath in an argon atmosphere, 1.4 ml of about 1.65M hexane solution of BuLi (0.00206×1.1 mol) was added thereto, followed by stirring for about 10 minutes. After 0.35 g (0.00206×2.0 mol) of isopropyl isocyanate dissolved in about 10 ml of diethyl ether was added to the reaction solution, the bath was removed and stirred at room temperature for about one hour. The reaction solution was mixed with about 5 ml of 1N aqueous hydrochloric acid solution, and then distributed with ethyl acetate-saturated sodium bicarbonate water, followed by washing with saturated brine. The organic phase of the obtained solution was dried with anhydrous sodium sulfate, concentrated and purified by using silica gel column chromatography (eluting solution: ethyl acetate/hexane) and reversed phase column (Lobor LiChroprep RP-10; eluting solution: acetonitrile/water), thereby obtaining an aimed product.

Yield by weight: 0.36 g; yield by percentage: 47%; solid; melting point: 66 to 69° C.; $^1$H-NMR (60 MHz, CDCl$_3$, δ): 1.09 (6H, d, J=6.4 Hz), 2.50 (3H, s), 3.6–4.4 (1H, mult.), 6.78 (1H, d, J=2 Hz), 6.8–7.7 (5H, complex), 7.72 (1H, d, J=2 Hz).

Production Example 15

Production of N-(i-propyl)-4-dimethylamino-6-{3-(trifluoromethyl)phenoxy}-2-pyridine carboxamide (compound No. I-38)

0.75 g (0.0021 mol) of 2-bromo-4-dimethylamino-6-{3-(trifluoromethyl)phenoxy} pyridine was suspended in about 15 ml of diethyl ether. While cooling the suspension in a dry ice-acetone bath in an argon atmosphere, 1.4 ml of about 1.65M hexane solution of BuLi (0.00206×1.1 mol) was added thereto, followed by stirring for about 10 minutes. After 0.35 g (0.00206×2.0 mol) of isopropyl isocyanate dissolved in about 10 ml of diethyl ether was added to the reaction solution, the bath was removed and stirred at room temperature for about one hour. The reaction solution was mixed with about 5 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by using silica gel column chromatography (eluting solution: ethyl acetate/hexane) and reversed phase column (Lobor LiChroprep RP-10; eluting solution: acetonitrile/water), thereby obtaining an aimed product.

Yield by weight: 0.22 g; yield by percentage: 29%; solid; melting point: 108 to 110° C.; $^1$H-NMR (60 MHz, CDCl$_3$, δ): 1.10 (6H, d, J=6.4 Hz), 3.00 (6H, s), 3.6–4.4 (1H, mult.), 6.06 (1H, d, J=2 Hz), 6.9–7.7 (6H, complex).

Production Example 16
Production of N-(i-propyl)-4-{methyl(phenylmethyl)amino}-6-{3-(trifluoromethyl)phenoxy}-2-pyridine carboxamide (compound No. I-39) 2.22 g (0.0051 mol) of 2-bromo-4-{methyl(phenylmethyl)amino}-6-{3-(trifluoromethyl)phenoxy} pyridine was suspended in about 30 ml of diethyl ether. While cooling the suspension in a dry ice-acetone bath in an argon atmosphere, 3.4 ml of about 1.65M hexane solution of BuLi (0.0051×1.1 mol) was added thereto, followed by stirring for about 10 minutes. After 0.86 g (0.0051×2.0 mol) of isopropyl isocyanate dissolved in about 10 ml of diethyl ether was added to the reaction solution, the bath was removed and stirred at room temperature for about one hour. The reaction solution was mixed with about 10 ml of 1N hydrochloric acid aqueous solution, and then distributed with ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 1.24 g; yield by percentage: 55%; oily substance; $^1$H-NMR (60 MHz, CDCl$_3$, δ): 1.09 (6H, d, J=6.4 Hz), 3.06 (6H, s), 3.6–4.4 (1H, mult.), 4.52 (2H, s), 6.09 (1H, d, J=2 Hz), 6.8–7.6 (11H, complex).

Various compounds (I) were produced by the processes according to the above-mentioned Production Examples 1 to 16. The obtained compounds according to the present invention are shown in Tables 2 to 7 below.

TABLE 2

| Compound No. | Z W$^{a)}$ | A$^{b)}$ X$_n^{b)}$ | R$_m^{c)}$ | Y$_p^{d)}$ | Yield (%) | Property (m.p. ° C.) |
|---|---|---|---|---|---|---|
| I-1 | O 4 | CHCH3 1-CH3 | — | — | 27 | Solid (105–107) |
| I-2 | O 2 | CHCH3 1-CH3 | 6-Br | — | 78 | Oily substance |
| I-3 | O 2 | CHCH3 1-CH3 | 4-CH3 | — | 82 | Oily substance |
| I-4 | O 3 | CHCH3 1-CH3 | 4-Cl | — | 39 | Solid (96–98) |
| I-5 | O 2 | Ph — | 4-OCH3 6-Br | — | 70 | Solid (145–147) |
| I-6 | O 2 | Ph 4-CH3 | 4-SCH3 6-Br | — | 51 | Solid (145–149) |
| I-7 | O 2 | Ph 4-CH3 | 4-OCH3 6-Br | — | 57 | Solid (153–157) |
| I-8 | O 2 | Ph — | 4-OCH2CH3 6-Br | — | 80 | Solid (91–95) |
| I-9 | O 2 | CH2Ph | 4-OCH3 6-Br | — | 86 | Solid (107–111) |

TABLE 3

| Compound No. | Z W$^{a)}$ | A$^{b)}$ X$_n^{b)}$ | R$_m^{c)}$ | Y$_p^{d)}$ | Yield (%) | Property (m.p. ° C.) |
|---|---|---|---|---|---|---|
| I-10 | O 2 | CHCH3 1-CH3 | 4-OCH3 6-Br | — | 74 | Solid (70–76) |
| I-11 | O 2 | CH2CH2CH2CH3 — | 4-OCH3 6-Br | — | 82 | Solid (44–48) |
| I-12 | O 2 | CH2CH2CH3 — | 4-OCH3 6-Br | — | 70 | Oily substance |
| I-13 | S 2 | CH2CH3 — | 4-OCH3 6-Br | — | 68 | Solid (59–62) |
| I-14 | O 2 | Ph — | 4-OCH3 6-OPh | 3-CF3 | 51 | Solid (140–142) |
| I-15 | O 2 | Ph 4-Cl | 4-OCH3 6-OPh | 3-CF3 | 56 | Solid (120–122) |
| I-16 | O | Ph | 4-OCH3 | 3-CF3 | 57 | Solid |

TABLE 3-continued

| Compound No. | Z W[a] | A[b] X_n[b] | R_m[c] | Y_p[d] | Yield (%) | Property (m.p. ° C.) |
|---|---|---|---|---|---|---|
| | | 2 | 3-CH3 | 6-OPh | | (145–146) |
| I-17 | O | Ph | 4-OCH3 | 3-CF3 | 46 | Solid |
| | | 2 | 4-OCH3 | 6-OPh | | (148–149) |
| I-18 | O | Ph | 4-OCH3 | 3-CF3 | 40 | Solid |
| | | 2 | 4-SCH3 | 6-OPh | | (115–116) |

TABLE 4

| Compound No. | Z W[a] | A[b] X_n[b] | R_m[c] | Y_p[d] | Yield (%) | Property (m.p. ° C.) |
|---|---|---|---|---|---|---|
| I-19 | O | Ph | 4-OCH3 | 3-CF3 | 60 | Solid |
| | | 2 | 3-CF3 | 6-OPh | | (135–137) |
| I-20 | O | Ph | 4-OCH3 | 3-CF3 | 55 | Solid |
| | | 2 | 4-F | 6-OPh | | (133–135) |
| I-21 | O | Ph | 4-OCH3 | 3-CF3 | 52 | Solid |
| | | 2 | 2,4-F2 | 6-OPh | | (135–137) |
| I-22 | S | Ph | 4-OCH3 | 3-OCHF2 | 42 | Solid |
| | | 2 | — | 6-OPh | | (101–104) |
| I-23 | O | Ph | 4-OCH3 | 3-OCF3 | 67 | Solid |
| | | 2 | — | 6-OPh | | (95–98) |
| I-24 | O | Ph | 4-SCH3 | 3-CF3 | 59 | Solid |
| | | 2 | — | 6-OPh | | (131–133) |
| I-25 | O | Ph | 4-N(CH3)2 | 3-CF3 | 62 | Solid |
| | | 2 | — | 6-OPh | | (135–138) |
| I-26 | S | Ph | 4-OCH3 | 3-CF3 | 57 | Solid |
| | | 2 | — | 6-OPh | | (126–128) |
| I-27 | O | Ph | 4-N(CH3)CH2Ph | 3-CF3 | 47 | Solid |
| | | 2 | — | 6-OPh | | (111–114) |

TABLE 5

| Compound No. | Z W[a] | A[b] X_n[b] | R_m[c] | Y_p[d] | Yield (%) | Property (m.p. ° C.) |
|---|---|---|---|---|---|---|
| I-28 | S | Ph | 4-OCH3 | 3-CF3 | 38 | Solid |
| | | 2 | 4-Cl | 6-OPh | | (130–132) |
| I-29 | O | Ph | 4-OCH3 | 3-CF3 | 27 | Solid |
| | | 2 | 4-Br | 6-OPh | | (103–108) |
| I-30 | O | (CH2)2CH3 | 4-OCH3 | 3-CF3 | 80 | Solid |
| | | 2 | — | 6-OPh | | (60–64) |
| I-31 | S | (CH2)2CH3 | 4-OCH3 | 3-CF3 | 76 | Solid |
| | | 2 | — | 6-OPh | | (91–93) |
| I-32 | O | CH2CH2 | 4-OCH3 | 3-CF3 | 52 | Solid |
| | | 2 | 2-Cl | 6-OPh | | (64–68) |
| I-33 | O | CCH3 | 4-OCH3 | 3-CF3 | 80 | Solid |
| | | 2 | 1,1-(CH3)2 | 6-OPh | | (110–115) |

TABLE 6

| Compound No. | Z W[a] | A[b] X_n[b] | R_m[c] | Y_p[d] | Yield (%) | Property (m.p. ° C.) |
|---|---|---|---|---|---|---|
| I-34 | O | CH2CH=CH2 | 4-OCH3 | 3-CF3 | 73 | Oily |
| | | 2 | — | 6-OPh | | substance |
| I-35 | O | cyclohexyl | 4-OCH3 | 3-CF3 | 63 | Solid |
| | | 2 | — | 6-OPh | | (111–115) |
| I-36 | S | CH2CH3 | 4-OCH3 | 3-CF3 | 61 | Solid |
| | | 2 | — | 6-OPh | | (112–116) |
| I-37 | O | CHCH3 | 4-SCH3 | 3-CF3 | 47 | Solid |
| | | 2 | 1-CH3 | 6-OPh | | (66–69) |
| I-38 | O | CHCH3 | 4-N(CH3)2 | 3-CF3 | 29 | Solid |
| | | 2 | 1-CH3 | 6-OPh | | (108–110) |
| I-39 | O | CHCH3 | 4-N(CH3)CH2Ph | 3-CF3 | 55 | Oily |

TABLE 6-continued

| Compound No. | Substituents | | | | Property | |
| --- | --- | --- | --- | --- | --- | --- |
| | Z W[a)] | A[b)] X$_n$[b)] | R$_m$[c)] | Y$_p$[d)] | Yield (%) | (m.p. °C.) |
| I-40 | 2 O 2 | 1-CH3 CH3 — | 6-OPh 4-OCH2CH3 6-OPh | 3-CF3 | 43 | substance Solid (65–67) |

TABLE 7

| Compound No. | Substituents | | | | Yield (%) | Property (m.p. °C.) |
| --- | --- | --- | --- | --- | --- | --- |
| | Z W[a)] | A[b)] X$_n$[b)] | R$_m$[c)] | Y$_p$[d)] | | |
| I-41 | O 2 | CHCH3 1-CH3 | 4-OCH2CH3 6-OPh | 3-CF3 | 55 | Solid (66–68) |
| I-42 | O 2 | CH2CH3 — | 4-OCH3 6-OPh | 3-CF3 | 74 | Solid (81–82) |
| I-43 | O 2 | CH3 — | 4-OCH3 6-OPh | 3-CF3 | 56 | Solid (123–125) |
| I-44 | S 2 | CH3 — | 4-OCH3 6-OPh | 3-CF3 | 69 | Solid (124–127) |

Note of Tables 2 to 7.
[a)]: Each number represents a bonding position where the carboxamide or thiocarboxamide moiety of each compound is bonded to the pyridine ring;
[b)]: The symbol "Ph" represents a phenyl group.

In the case where A has substituents thereon, the number prefixed to the en dash (–) represents a bonding position of each substituent, and the number suffixed to the en dash (–) represents the number of bonding positions when the same kind of 2 or more substituents are present.

"4-Cl" of the compound (I-15) indicates that one Cl (chloro) is bonded to the 4-position of phenyl ring, and "2,4-F2" of the compound (I-21) indicates that "F"s (fluoro) are bonded to two positions, i.e., the 2- and 4-positions of phenyl ring.

"CH2CH2" of the compound (I-32) indicates that one of carbon atoms of $CH_2CH_2$ which is unsaturated with respect to bonding number, is bonded to a nitrogen atom of 2-CONH of pyridine, and the other carbon atom is bonded to X$_n$, and "2-Cl" indicates that Cl is bonded to the 2-position carbon atom, assuming that the carbon atom of $CH_2CH_2$ which is bonded to the nitrogen atom of 2-CONH of pyridine, is in the 1-position.

"CCH3" of the compound (I-33) indicates that the carbon atom which is unsaturated in bonding number, is bonded to the nitrogen atom of 2-CONH of pyridine, and the same carbon atom is also bonded to X$_n$. "1,1-(CH3)2" of the compound (I-33) indicates that two $CH_3$ groups are bonded to the above-mentioned carbon atom. Thus, in the case where A is represented by only carbon atoms and hydrogen atoms, the carbon atom bonded to the nitrogen atom of 2-CONH of pyridine or X$_n$ is indicated in such a condition as unsaturated with respect to bonding number thereof.

The em dash (—) means an unsubstituted condition (n=0).

c): With respect to R, the number prefixed to the en dash (–) represents a bonding position thereof.

d): Yp represents a substituent bonded to the benzene ring in the case where R is a phenoxy group. The regularities of Y$_p$ are the same as those of X$_n$ in the case of A=Ph.

INDUSTRIAL APPLICABILITY

As described above, the process for the production of N-substituted pyridine carboxamide or thiocarboxamide according to the present invention can be applied even to such compounds having oxidation-susceptible substituent groups, and it is not necessary to produce substituted or unsubstituted pyridine thiocarboxamide from corresponding substituted or unsubstituted pyridine carboxamide. Therefore, the process of the present invention is industrially useful.

What is claimed is:

1. A process for producing N-substituted-(substituted or unsubstituted) pyridine carboxamide or thiocarboxamide, comprising reacting a substituted or unsubstituted pyridine metal compound with substituted isocyanate or thioisocyanate to obtain an addition reaction product thereof, and then substituting the metal of said addition reaction product with a proton.

2. A process according to claim 1, wherein N-substituted pyridine carboxamide or thiocarboxamide represented by the general formula (I) is produced by reacting a pyridine metal compound represented by the general formula (II) with substituted isocyanate or isothiocyanate to obtain an addition reaction product thereof, and then substituting the metal of said addition reaction product with a proton,

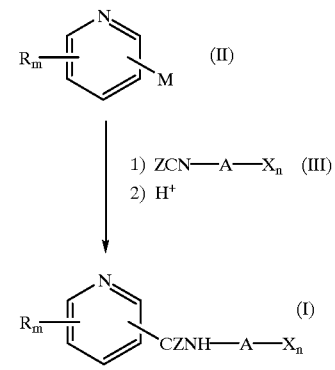

wherein R is a hydrogen atom, a halogen atom, an alkyl group, a haloalkyl group, an alkoxy group, a haloalkoxy group, an alkylthio group, a haloalkylthio group, a dialkylamino group, a (substituted or unsubstituted) phenoxy group, a (substituted or unsubstituted) phenylthio group, a di{(substituted or unsubstituted)phenyl}amino group, an alkyl{(substituted or unsubstituted)phenyl}amino group, an alkyl{(substituted or unsubstituted)phenylalkyl}amino group or a {(substituted or unsubstituted)phenyl} {{substituted or unsubstituted)phenyl}alkyl}amino group;

m is an integer of 0 to 4, and when m is an integer of not less than 2, Rs may be the same or different;

A is an alkyl group, an alkenyl group, an alkynyl group, a cycloalkyl group, a cycloalkylalkyl group, a phenyl group or an aralkyl group;

X is a halogen atom, an alkoxy group, a haloalkoxy group, an alkylthio group, an alkyl group, a haloalkyl group or a di(alkyl)amino group;

n is 0 to an integer selected from numbers of hydrogen atoms which can be substituted with hydrocarbon groups, and when n is an integer of not less than 2, Xs may be the same or different;

Z is an oxygen atom or a sulfur atom; and

M is alkali metal, alkali earth metal-Q wherein Q is a halogen atom, or ½(Cu-alkali metal).

3. A process according to claim 1, wherein said metal is lithium.

* * * * *